(12) United States Patent
Fujimori et al.

(10) Patent No.: US 6,197,029 B1
(45) Date of Patent: Mar. 6, 2001

(54) INTRAMEDULLARY NAIL

(76) Inventors: Juhro Fujimori, 3-2-501, Sengoku 1-Chome, Koto-ku, Tokyo 135; Shinichi Yoshino, 35-14, Asahicho 2-Chome, Nerima-ku, Tokyo 179; Masahito Koiwa, 56-16-703, Chuo 1-Chome, Kasukabe-shi, Saimata 344, all of (JP)

( * ) Notice: Subject to any disclaimer, the term of this patent is extended or adjusted under 35 U.S.C. 154(b) by 0 days.

(21) Appl. No.: 09/155,691
(22) PCT Filed: Apr. 5, 1996
(86) PCT No.: PCT/JP96/00946
  § 371 Date: Dec. 1, 1998
  § 102(e) Date: Dec. 1, 1998
(51) Int. Cl.[7] ............................ A61B 17/72; A61B 17/78
(52) U.S. Cl. ......................................................... 606/62
(58) Field of Search ..................... 606/62, 67, 73

(56) References Cited

U.S. PATENT DOCUMENTS

| 3,990,438 | * | 11/1976 | Pritchard | 606/73 |
| 4,261,351 | * | 4/1981 | Scherfel | 606/62 |
| 5,034,013 | * | 7/1991 | Kyle et al. | 606/62 |
| 5,053,035 | * | 10/1991 | McLaren | 606/62 |
| 5,454,813 | * | 10/1995 | Lawes | 606/62 |
| 5,561,437 | * | 2/1971 | Orlich | 606/67 |
| 5,766,174 | * | 6/1998 | Perry | 606/62 |

FOREIGN PATENT DOCUMENTS

07222753 * 8/1995 (JP) ........................................ 606/62

* cited by examiner

*Primary Examiner*—Paul J. Hirsch
(74) *Attorney, Agent, or Firm*—Koda & Androlia

(57) ABSTRACT

An intramedullary nail in which a plurality of fins (26) which protrude radially are formed on the outer circumference of the nail, providing firm internal fixation which makes the nail easy to operate.

2 Claims, 4 Drawing Sheets

INTRAMEDULLARY NAIL

TECHNICAL FIELD

The present invention relates to an intramedullary nail which can be suitably used for the purpose of fixating of joints and fracture locations, and more specifically for the purpose of arthrodesis of the ankle joint.

BACKGROUND TECHNOLOGY

Intramedullary nails are considered to be effective for internal fixation in the treatment of fractures, etc.; and recently, the use of such nails has become common. Specifically, in this method, the intramedullary nail is inserted into the bone marrow through the fracture site, and internal fixation is accomplished by passing at least two transfixation screws through screw holes formed in the intramedullary nail on both sides of the fracture site. In this method, however, depending on the location of the fracture, there may be cases in which the transfixation screws do not pass through.

Meanwhile, the destruction of the ankle joint is also common in patient with rheumatoid arthritis, etc. In such cases, arthrodesis of the ankle joint is considered to be effective. However, arthrodesis of the ankle joint is extremely difficult. Therefore, there are several conventionally utilized methods to fix these joints, and these include the following: 1) Methods in which cancellous screws are passed obliquely through the tibia and screwed into the talus or calcaneus. 2) Methods in which a plate is positioned along the talus, tibia and/or calcaneus and fixed using screws. 3) Methods in which pins are inserted in the tibia, talus and/or calcaneus, and then fixed to an external fixation device.

However, one problem that is common to these methods is that fixation is not rigid. In particular, they do no sufficiently control rotation and bending of the ankle joint. As a result, long period of immobilization without weight-bearing is required after surgery. Furthermore, in cases where an external fixation device is used, the pin insertion areas tend to become contaminated, so that repeated dressings is required.

Meanwhile, arthrodesis of the ankle joint, the use of conventional intramedullary nails is also considered. However, even if used in combination with transfixation screw, intramedullary nails do not sufficiently control rotation, pronation and supination, and dorsal and plantar flexion of the ankle-joint, particularly in patients with rheumatoid arthritis who have osteoporotic bone.

The present invention solves such problems. In short, the object of the present invention is to provide an intramedullary nail which makes it possible to obtain a firm fixation and which can easily perform operation.

DISCLOSURE OF THE INVENTION

In view of the object described above, the intramedullary nail of the present invention is characterized by the fact that a plurality of fins which protrude radially are formed on the outer circumference of the nail. Furthermore, the intramedullary nail of the present invention is characterized by the fact that in this construction, a screw hole is formed in the distal end, and a screw which has a large-diameter head part is screwed into this hole.

As a result of the adoption of the above-described means, the plurality of fins formed on the intramedullary nail act as a resistance to bone marrow and cortical bone, so that the movement of joints and the fracture can be prevented. In particular, the checking force with respect to any rotational force is strong; and in this regard, the present invention is extremely effective for arthrodesis of the joints. Furthermore, since these fins serve as substitutes for transfixation screws, the transfixation screws conventionally considered necessary are no longer needed.

Meanwhile, by the use of the screw with a large-diameter head which is screwed into the screw hole formed in the distal end of intramedullary nail, joints or bones clamped between the intramedullary nail and the screw can be tightened, thereby strengthen the fixing force. This fixing force can be adjusted to a wide extent by this tightening, which can be done even with preliminary pressure being applied.

BEST MODE TO CARRY OUT THE INVENTION

Figure 5:
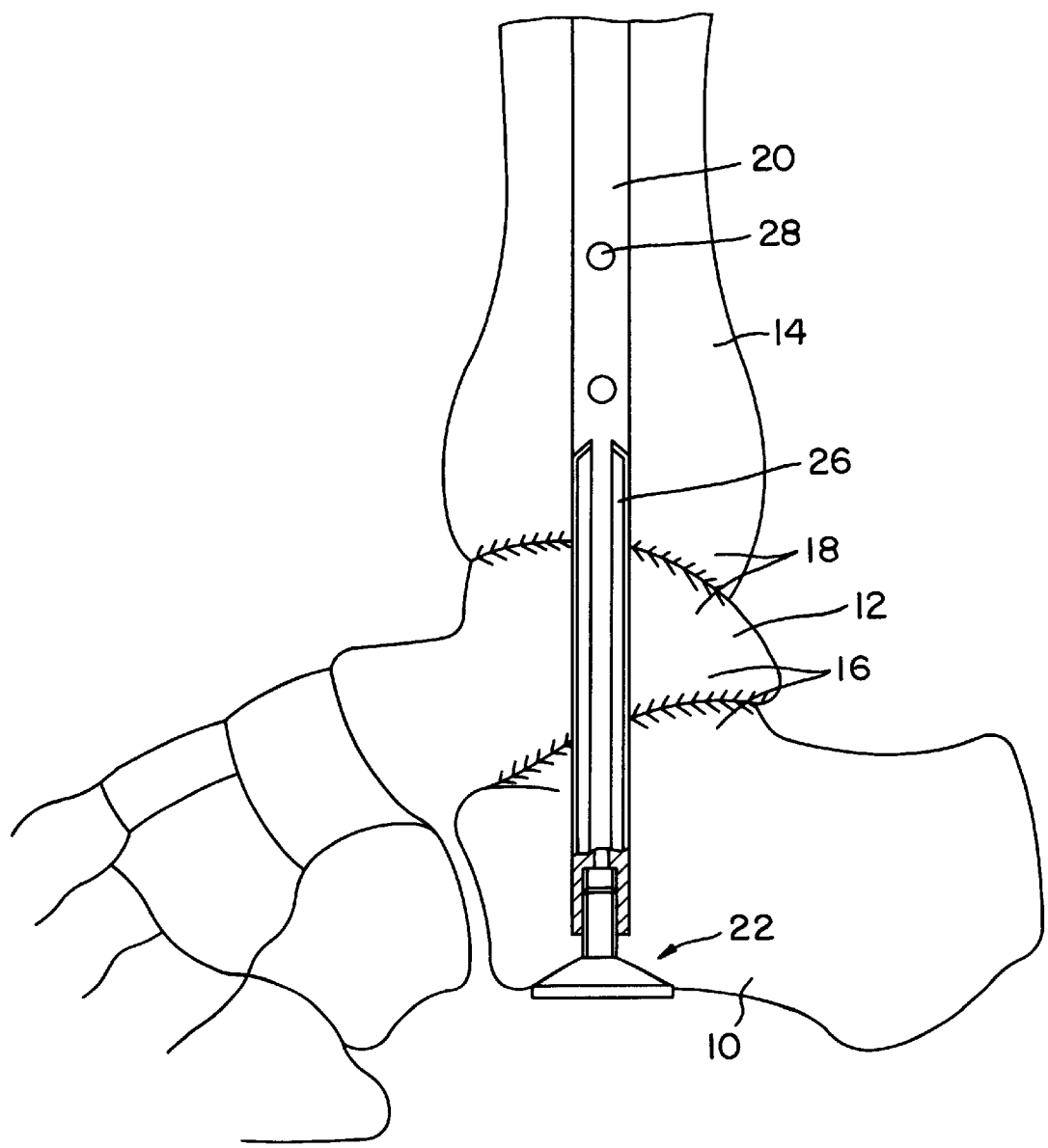
FIG. 5 is an explanatory diagram which illustrates the conditions of use of the intramedullary nail of the present invention.

A case in which the ankle joint is under arthrodesis using the intramedullary nail of the present invention will be described below with reference to the attached figures. FIG. 5 is a model diagram which shows the skeletal structure of the foot. The bones of the foot are connected in order, from the bottom, of the calcaneus 10, talus 12 and tibia 14. The articular surfaces of the calcaneus 10 and the talus 12, and the articular surfaces of the talus 12 and the tibia 14 form joints 16 and 18, respectively.

Figure 1:
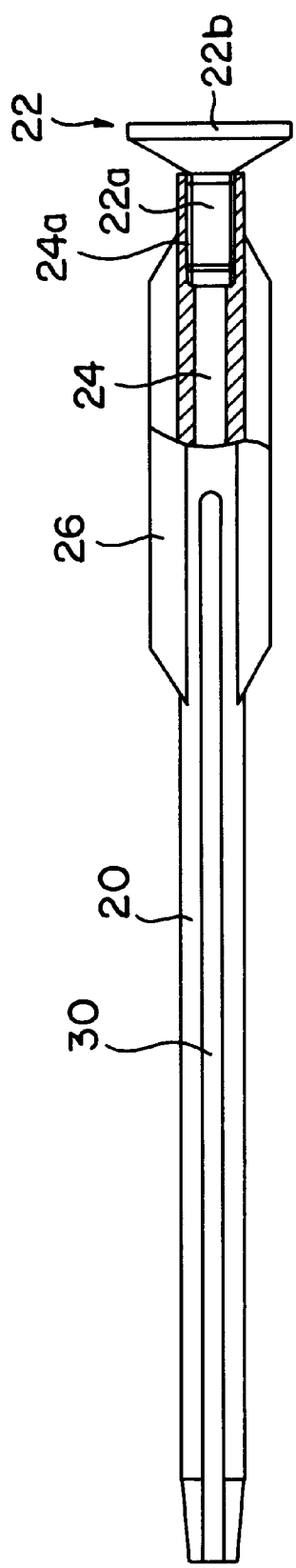
FIG. 1 is a side view which illustrates an embodiment of the intramedullary nail of the present invention.
Figure 2:
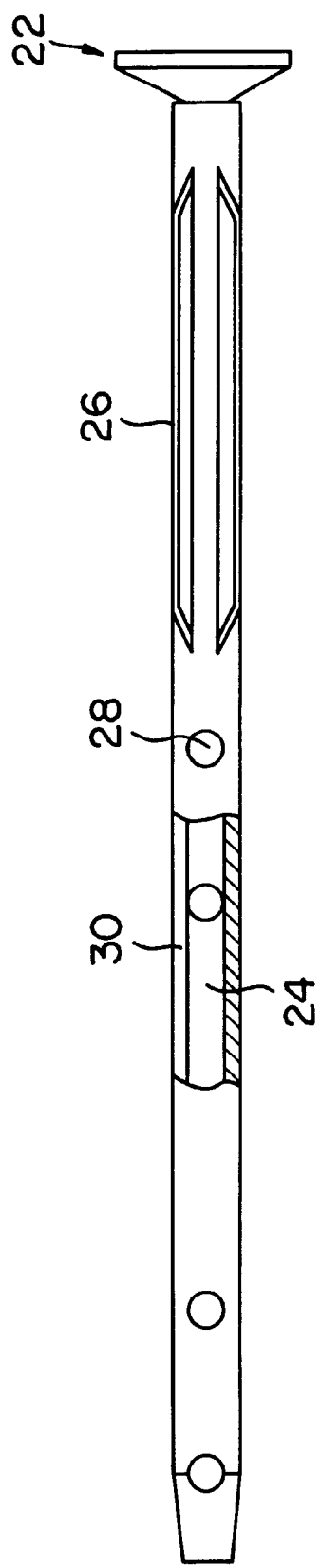
FIG. 2 is a side view which illustrates an embodiment of the intramedullary nail of the present invention.

FIGS. 1 and 2 are partial section side views of the intramedullary nail of the present invention. As in conventional intramedullary nails, this intramedullary nail 20 has a rod-form body with a hollow portion 24 inside; and the characterizing feature of this intramedullary nail 20 is that a plurality of fins 26 are formed on the outer circumference of the nail. The intramedullary nail 20 is made of a metal, e.g., a titanium alloy, etc., which does not have a deleterious effect on marrow tissues and does not generate any rust, etc.

Figure 3:
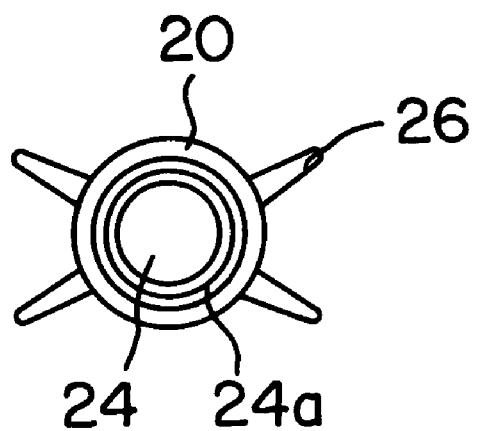
FIG. 3 is an enlarged distal end view which illustrates an embodiment of the intramedullary nail of the present invention.

FIG. 3 is an enlarged distal end view of the intramedullary nail 20. In this example, four fins with sharp tips 26 which extend from the distal part of the intramedullary nail 20 to an intermediate part are formed at unequal intervals. The external diameter of the fins 26 is 1.5 to 2 times the external diameter of the intramedullary nail 20. Furthermore, the length along which the fins 26 are formed is approximately 20 to 40% of the total length of the nail. However, these values are merely examples; and the spacing, number (a plurality of fins must be formed), amount of protrusion, length of formation, etc. of the fins 26 are not limited to the values shown.

Figure 4:
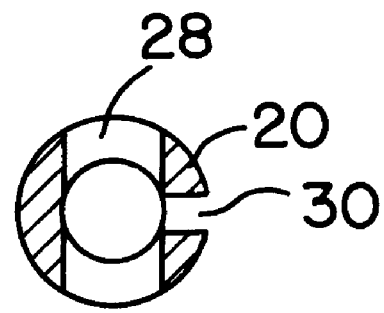
FIG. 4 is an enlarged cross-sectional proximal part view which illustrates an embodiment of the intramedullary nail of the present invention.

FIG. 4 is an enlarged cross-sectional proximal part view of the intramedullary nail 20. Screw-holes 28, through which transfixation screws (not shown in any of these figures) are inserted and passed horizontally through the center of the nail, are also formed at appropriate intervals in the intramedullary nail 20. Furthermore, a split groove 30 is formed from the proximal end toward the distal part, and this split groove 30 is positioned 90° from the location of screw-holes 28. This split groove 30 is for allowing the flow of marrow tissues between the inside and outside of the intramedullary nail 20. It has been confirmed that this promotes the healing effect. However, this split groove is not an absolute requirement; and in small nails, this may not be formed.

A screw hole 24a is formed in the distal part (distal end) of the hollow section 24 in the intramedullary nail 20. A screw 22 is screwed into this screw hole 24a. The screw 22 has a dish-shaped large-diameter head portion 22b on a threaded trunk portion 22a. This screw 22 is also made of a non-rusting material such as a titanium alloy, etc.

A case in which the foot joints 16 and 18 are arthrodesed using the above-described intramedullary nail 20 will be described with reference to FIG. 5. First, from the bottom of the calcaneus 10, the intramedullary nail 20 is inserted longitudinally to the centers of the talus 12 and tibia 14. In this case, the nail 20 is adjusted so that the fins 26 are present across the foot joint 16 and 18.

Next, transfixation screws (not shown in the figures) are inserted into the screw-holes 28 in the intramedullary nail 20 at least in the tibia 14 located at the proximal part, and fastened by being screwed into the outer bone cortex. The screw 22 is screwed into the intramedullary nail 20 where it is then tightened and fastened by the head portion 22b (see FIG. 1). This puts pressure on the respective joints 16 and 18 and prevent them from moving. As a result, the fins 26 and screw 22 act as substitutes for the transfixation screws, so that the foot joints are rigidly fixed and do not become loose during daily use after surgery. In particular, because of the fins 26, any force that would tend to cause the respective bones 10, 12 and 14 to rotate relative to each other is firmly checked, thus providing firm internal fixation. In unlikely event that there should be any weakening, the fixing force can be restored by a follow-up tightening of the screw 22.

The above description is made for the case in which the joints of the foot are fixed in place. However, since the intramedullary nail of the present invention is inserted from the calcaneus, this nail can also be used in fractures of the tibia in cases where a total knee arthroplasty has been performed. This stands in contract to conventional intramedullary nails, which cannot be used in such cases. The intramedullary nail of the present invention is particularly useful in cases where there is also destruction of an ankle and subtalar joint, rheumatoid arthritis, etc., the intramedullary nail of the present invention can be used to fix tibial fracture along with arthrodesis of these joints.

Furthermore, in the case of supracondylar fracture of the femur that would occur following total knee arthroplasty, there has been no effective internal fixation method in the past. However, such internal fixation can also be accomplished by using the intramedullary nail of the present invention. It can be accomplished by opening the knee joint, inserting the intramedullary nail from the lower end of the femur, and screwing transfixation screws.

POSSIBILITIES OF UTILIZATION IN THE INDUSTRY

Thus, in the present invention, fins formed on the intramedullary nail act as a resistance with respect to bone marrow and cortical bone, so that the movement of joints and the movement of bones relative to each other can be prevented. In particular, a strong stopping force can be manifested with respect to rotational and bending forces. Furthermore, since joints and bones can be clamped between the intramedullary nail and screw with a large-diameter head, the movement of joints and the movement of bones relative to each other can be restricted even further. In addition, the number of tansfixation set screws that are passed through screw-holes are small, and can be reduced in the intramedullary nail of the present invention; accordingly, operation is quick and easy.

What is claimed is:

1. An intramedullary nail comprising an intermudullary nail body and a screw, wherein:
    said intramedullary nail body, which is inserted into a meudlla, is provided with:
        a hollow portion inside said nail body,
        a plurality of fins radially projecting on an outer surface of said nail body, said fins only extending for a predetermined length from one end of said nail body,
        screw holes formed in areas in which said fins are not formed and extending at right angles axis of said nail body, and
        a screw hole formed in said one end of said nail body; and
    said screw, which is inserted into a bone end and screw-engaged with said screw hole of said nail body, is provided with a tapered body.

2. The intramedullary nail according to claim 1, further comprising a split groove that extends parallel to said axis of said nail body and communicates with said hollow portion of said nail body.

* * * * *